(12) United States Patent
Choi

(10) Patent No.: US 10,390,792 B2
(45) Date of Patent: Aug. 27, 2019

(54) ULTRASONIC DIAGNOSIS DEVICE AND METHOD OF DIAGNOSING BY USING THE SAME

(71) Applicant: SAMSUNG MEDISON CO., LTD., Gangwon-do (KR)

(72) Inventor: Doo-hyun Choi, Gangwon-do (KR)

(73) Assignee: SAMSUNG MEDISON CO., LTD., Hongcheon-gun, Gangwon-do (KR)

( * ) Notice: Subject to any disclaimer, the term of this patent is extended or adjusted under 35 U.S.C. 154(b) by 148 days.

(21) Appl. No.: 14/714,244

(22) Filed: May 15, 2015

(65) Prior Publication Data

US 2015/0335315 A1  Nov. 26, 2015

(30) Foreign Application Priority Data

May 15, 2014 (KR) .................. 10-2014-0058398

(51) Int. Cl.
*A61B 8/00* (2006.01)
*A61B 8/13* (2006.01)

(52) U.S. Cl.
CPC .............. *A61B 8/4254* (2013.01); *A61B 8/13* (2013.01); *A61B 8/4263* (2013.01); *A61B 8/462* (2013.01)

(58) Field of Classification Search
CPC ....... A61B 8/4254; A61B 8/13; A61B 8/4263; A61B 8/462
See application file for complete search history.

(56) References Cited

U.S. PATENT DOCUMENTS

| 5,920,395 A | * | 7/1999 | Schulz | A61B 5/0064 356/141.1 |
|---|---|---|---|---|
| 2003/0144768 A1 | * | 7/2003 | Hennion | A61B 34/35 701/2 |
| 2005/0049495 A1 | * | 3/2005 | Sumanaweera | A61B 8/00 600/437 |
| 2005/0182316 A1 | * | 8/2005 | Burdette | A61B 8/0833 600/424 |
| 2007/0021738 A1 | * | 1/2007 | Hasser | A61B 8/4218 606/1 |
| 2012/0203107 A1 | * | 8/2012 | Kim | A61B 8/14 600/443 |
| 2013/0024213 A1 | | 1/2013 | Poon | |
| 2014/0171799 A1 | * | 6/2014 | Hershey | A61B 8/4254 600/440 |

FOREIGN PATENT DOCUMENTS

| JP | 2002-017732 A | 1/2002 |
|---|---|---|
| JP | 2004-062709 A | 2/2004 |
| JP | 2006-122078 A | 5/2006 |
| KR | 10-0319912 B1 | 4/2002 |

* cited by examiner

*Primary Examiner* — Tse W Chen
*Assistant Examiner* — Joanne M Hoffman
(74) *Attorney, Agent, or Firm* — Morgan, Lewis & Bockius LLP

(57) ABSTRACT

An ultrasonic diagnosis device includes an image generation unit configured to generate image data of a target object diagnosed by a first user; a location confirming unit configured to confirm first location information of a probe with respect to the target object; a communication unit configured to transmit the image data and the first location information and to receive second location information of an auxiliary probe with respect to an auxiliary target object; and a display configured to display a location correction display of the probe based on the second location information.

16 Claims, 14 Drawing Sheets

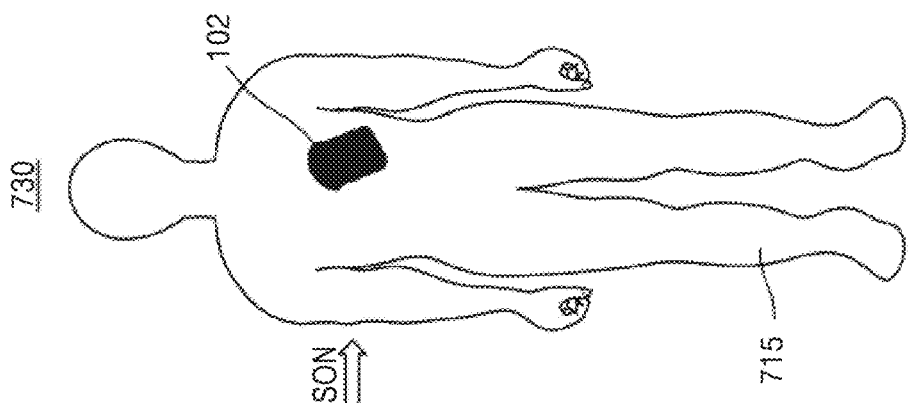
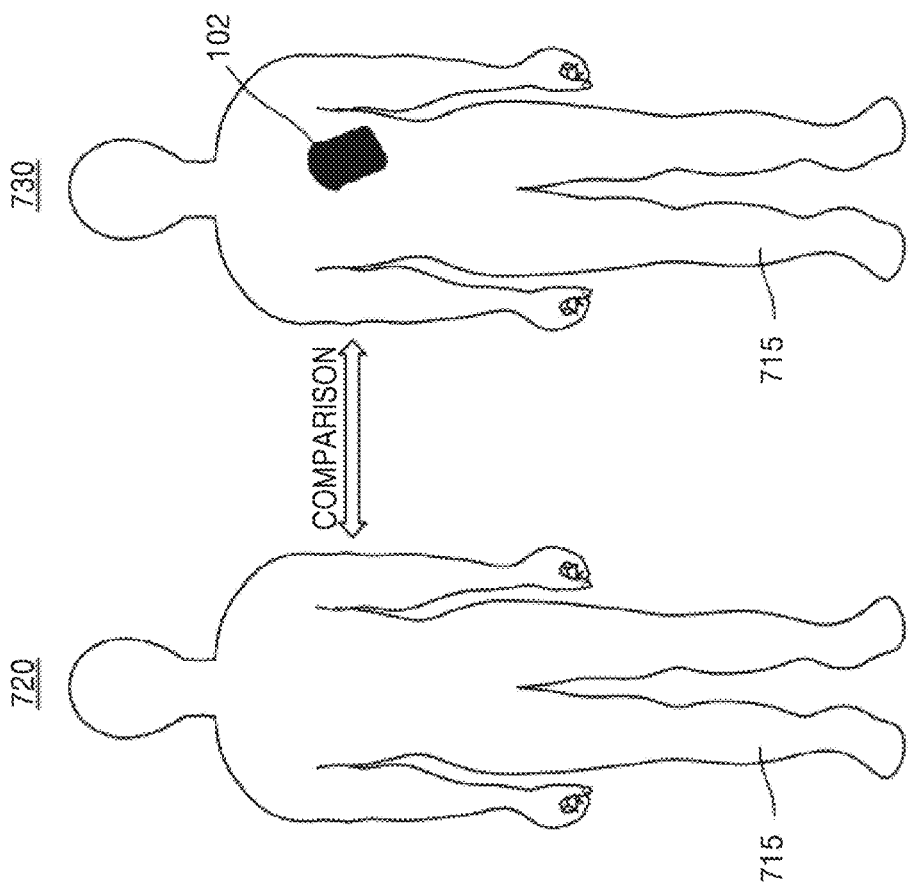
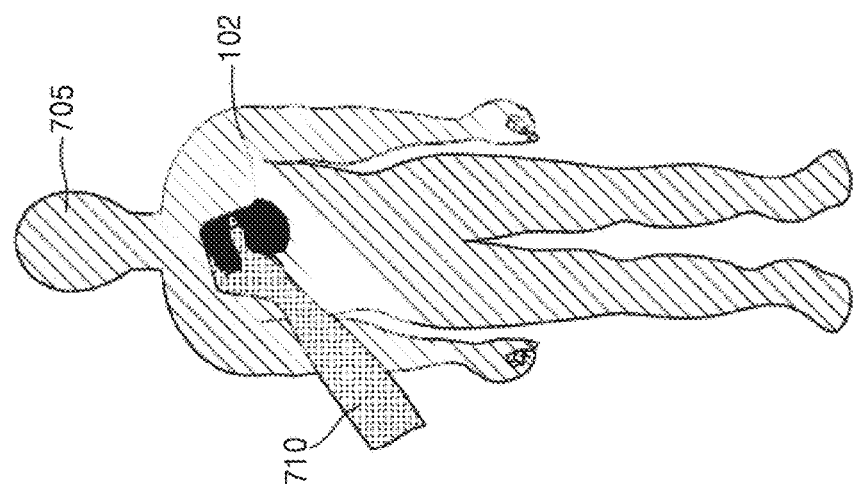

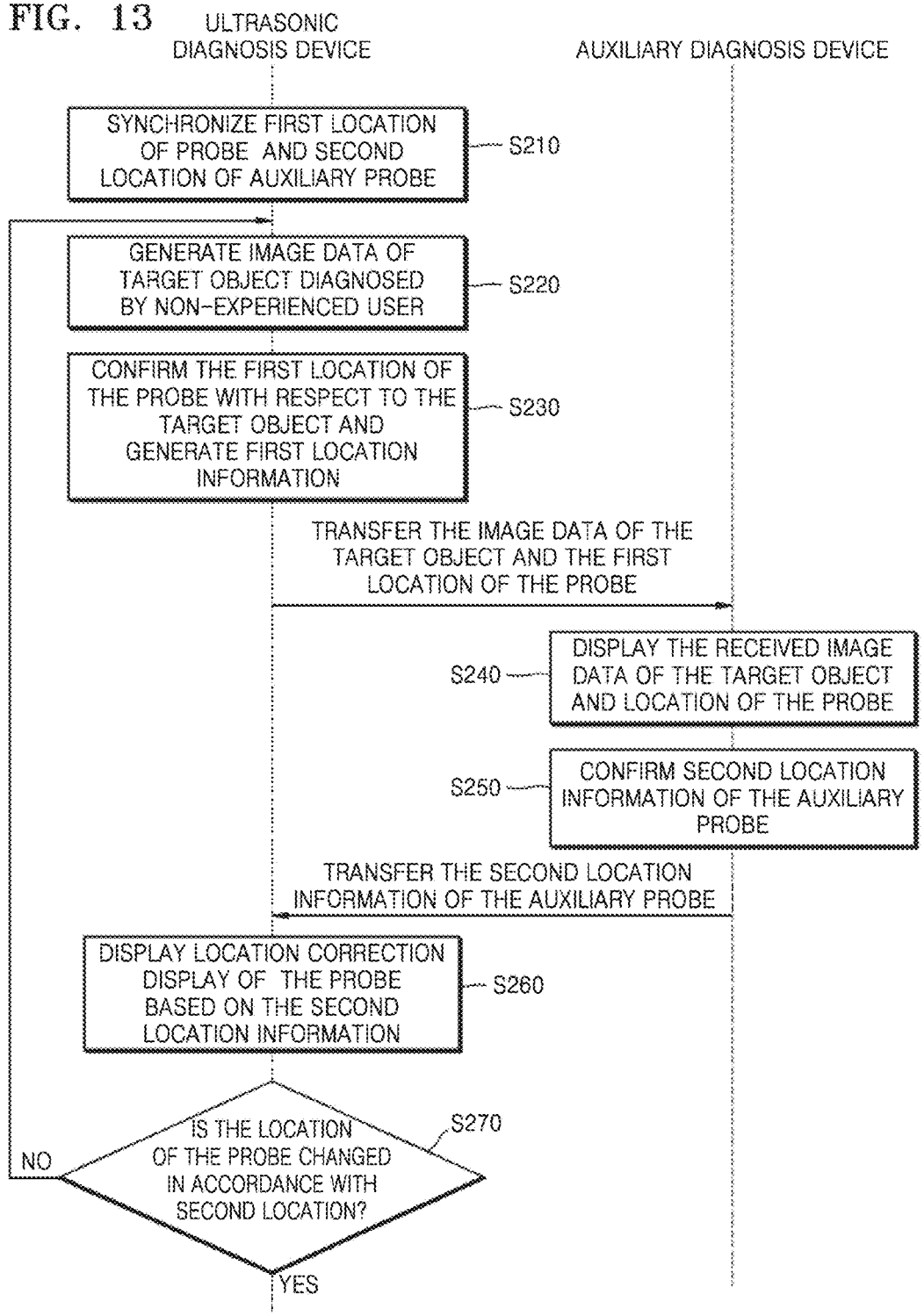

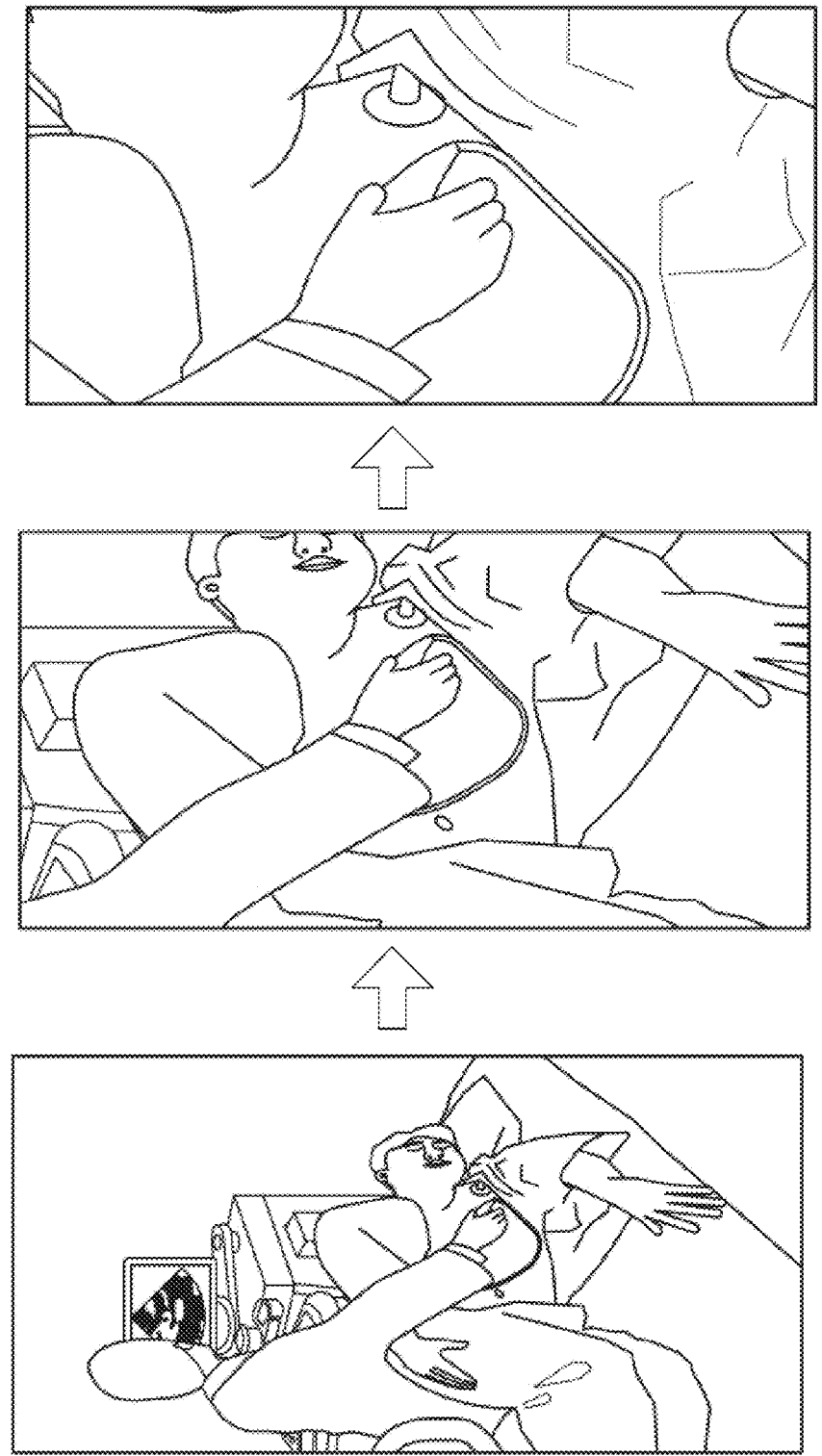

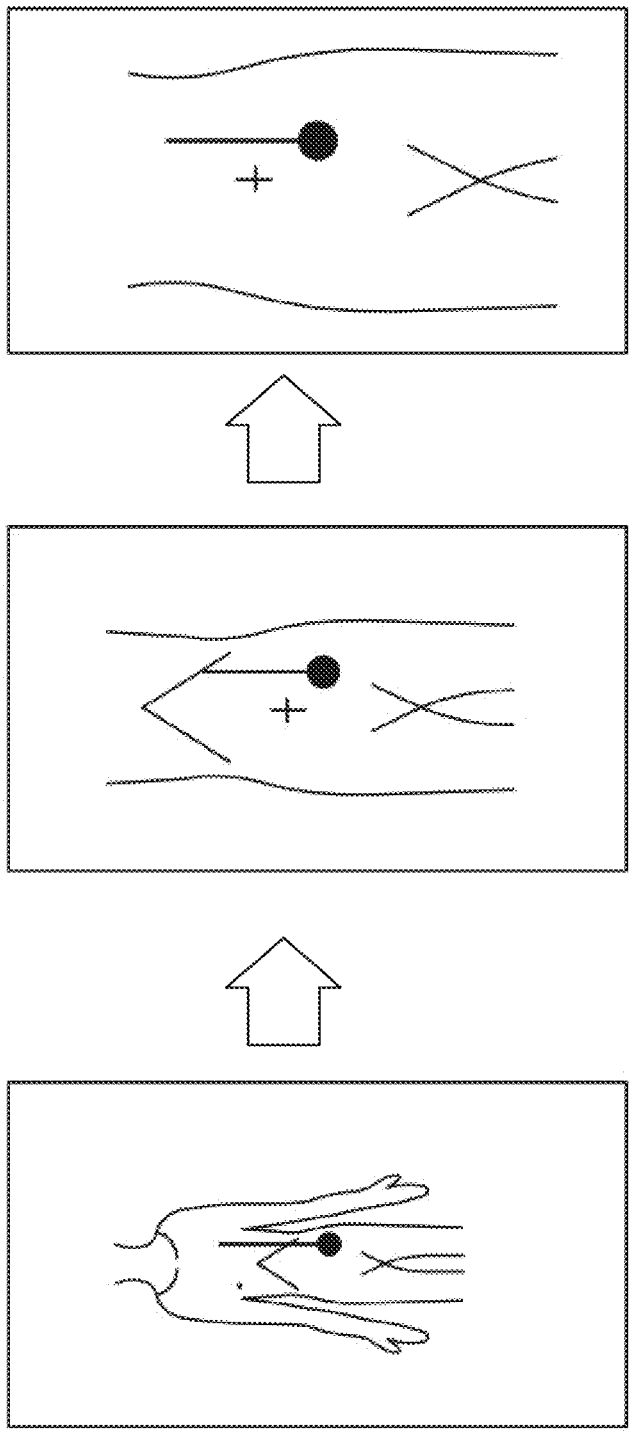

ULTRASONIC DIAGNOSIS DEVICE AND METHOD OF DIAGNOSING BY USING THE SAME

CROSS-REFERENCE TO RELATED PATENT APPLICATION

This application claims the benefit of Korean Patent Application No. 10-2014-0058398, filed on May 15, 2014, in the Korean Intellectual Property Office, the disclosure of which is incorporated herein in its entirety by reference.

BACKGROUND OF THE INVENTION

1. Field of the Invention

The present invention relates to an ultrasonic diagnosis device and a method of diagnosing by using the same, and more particularly, to an ultrasonic diagnosis device that enables a user to further facilitate ultrasonic diagnosis and a method of diagnosing by using the same.

2. Description of the Related Art

An ultrasonic diagnosis device irradiates ultrasonic signals generated by transducers of a probe to a target object and receives echo signals reflected from the target object, thereby obtaining images regarding the interior of the target object (e.g., tomography of soft tissues or blood flow). In particular, an ultrasonic diagnosis device may be used for medical purposes including observation of the interior of a target object, detection of foreign substances, and diagnosis of damage. Such an ultrasonic diagnosis device may display information regarding a target object in real-time. Furthermore, an ultrasonic diagnosis device causes no radioactive exposure like X-rays, and thus, is very safe. Therefore, an ultrasonic diagnosis device is widely used together with other types of imaging diagnosis devices.

Technologies for remotely performing ultrasonic diagnosis have been recently developed. In general, such remote diagnosis is performed by enabling an experienced person who is accustomed to the ultrasonic diagnosis to assist a non-experienced person who is not accustomed to the ultrasonic diagnosis in performing the ultrasonic diagnosis.

SUMMARY OF THE INVENTION

The present invention provides an ultrasonic diagnosis device for further facilitating ultrasonic diagnosis and a method of diagnosing the same.

According to an aspect of the present invention, there is provided an ultrasonic diagnosis device including: an image generation unit configured to generate image data of a target object diagnosed by a first user; a location confirming unit configured to confirm first location information of a probe with respect to the target object; a communication unit configured to transmit the image data and the first location information and to receive second location information of an auxiliary probe with respect to an auxiliary target object; and a display configured to display a location correction display of the probe based on the second location information.

The second location information may be determined according to a movement of the auxiliary probe adjusted by a second user.

The auxiliary probe may include a three-dimensional (3D) sensor that tracks a movement of the auxiliary probe.

The display may be included in at least one of the probe and a body of the ultrasonic diagnosis device.

The image data of the target object may be 3D image data.

The first location information of the probe may be a location of the target object with respect to a 3D image.

The ultrasonic diagnosis device may further include: a camera for enabling the first user to capture an image used to diagnose the target object in real time.

The communication unit may transmit the image to be used for diagnosis by the first user.

The camera may zoom in on the image to be used for diagnosis by the first user with respect to a location of the probe.

The communication unit may transmit the first location information of the probe in an image of the target object in real time.

The display may display the first location information of the probe and the second location information of the auxiliary probe.

The location correction display of the probe may display a location of the probe that needs to be corrected as at least one selected from the group consisting of a moving direction, a moving distance, a scan direction, a scan range, a rotation direction, and a rotation angle.

The communication unit may transmit and receive data to enable users to exchange information through at least one of a voice call and a conference call.

According to another aspect of the present invention, there is provided an ultrasonic diagnosis method including: generating image data of a target object; confirming first location information of a probe with respect to the target object; transmitting the image data and the first location information; receiving second location information of an auxiliary probe with respect to an auxiliary target object; and displaying a location correction display of the probe based on the second location information.

The second location information may be determined according to a movement of the auxiliary probe adjusted by a second user.

The image data of the target object may be 3D image data.

The first location information of the probe may be a location of the target object with respect to a 3D image.

The ultrasonic diagnosis method may further include: displaying the first location information of the probe and the second location information of the auxiliary probe.

The displaying of the location correction display of the probe may include displaying a location of the probe that needs to be corrected as at least one selected from the group consisting of a moving direction, a moving distance, a scan direction, a scan range, a rotation direction, and a rotation angle.

According to one or more embodiments of the present invention, there is provided a non-transitory computer-readable storage medium storing a computer program for executing the method.

BRIEF DESCRIPTION OF THE DRAWINGS

The above and other features and advantages of the present invention will become more apparent by describing in detail exemplary embodiments thereof with reference to the attached drawings in which:

FIGS. 6A through 6C are diagrams for explaining a process of acquiring location information of a probe, according to an embodiment of the present invention;

FIG. 13 is a flowchart for explaining operations of an ultrasonic diagnosis device and an auxiliary diagnosis device, according to an embodiment of the present invention; and FIGS. 14A-14C are diagrams for explaining a process of synchronizing a location of a probe and a location of an auxiliary probe, according to an embodiment of the present invention.

FIGS. 15A-15C are diagrams for explaining a process of synchronizing a location of a probe and a location of an auxiliary probe, according to an embodiment of the present invention.

DETAILED DESCRIPTION OF THE INVENTION

Figure 1:
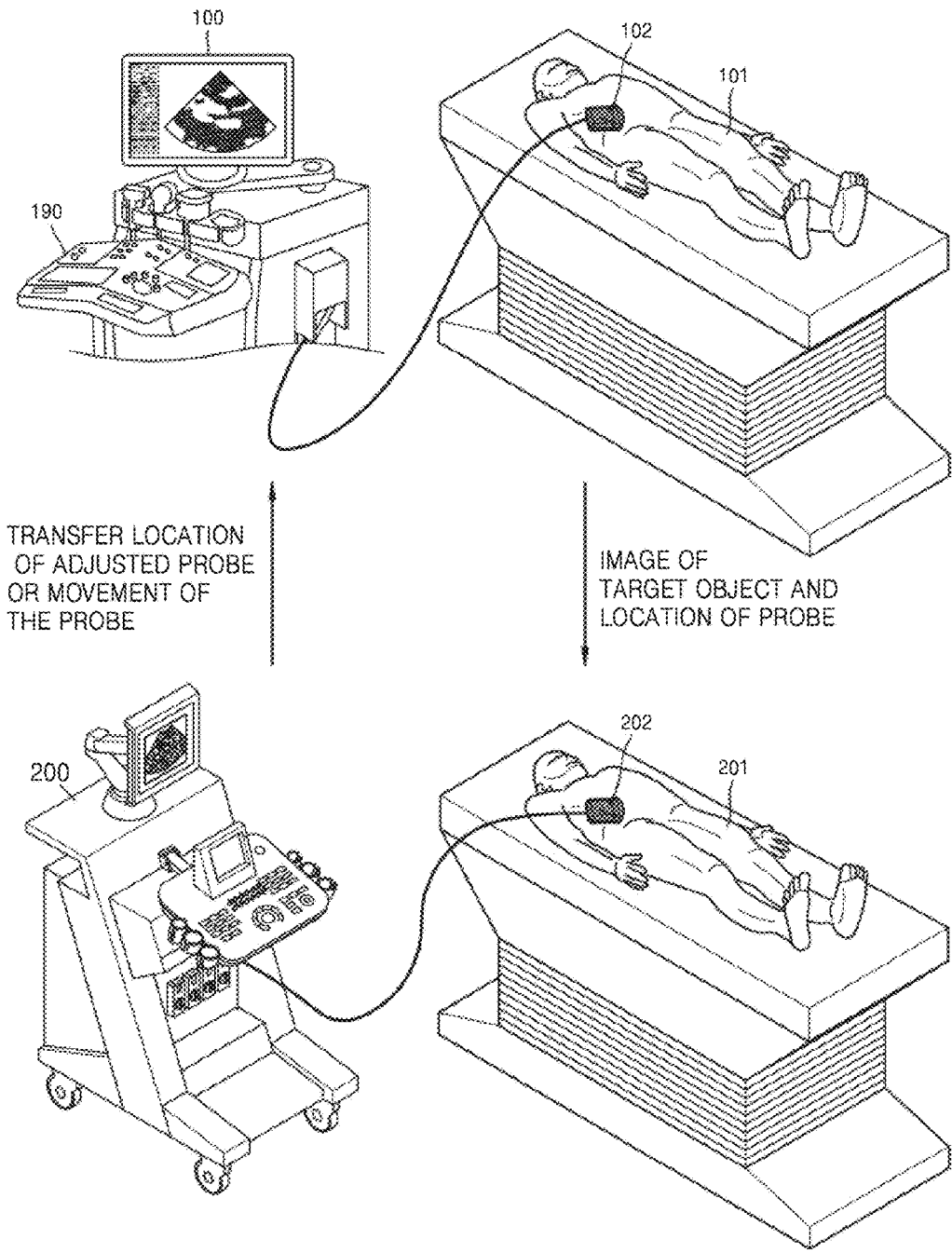
FIG. 1 illustrates an ultrasonic diagnosis device according to an embodiment of the present invention.

In the following detailed description, only certain exemplary embodiments of the present invention have been shown and described, simply by way of illustration. As those of ordinary skill in the art will realize, the described embodiments may be modified in various different ways, without departing from the spirit or scope of the present invention. Accordingly, the drawings and description are to be regarded as illustrative in nature and not restrictive. Like reference numerals designate like elements throughout the specification.

Throughout this specification and the claims that follow, when it is described that an element is "coupled" to another element, the element may be "directly coupled" to the other element or "electrically coupled" or "communicatively connected" to the other element through a third element. In addition, unless explicitly described to the contrary, the word "comprise" and variations such as "comprises" or "comprising", will be understood to imply the inclusion of stated elements but not the exclusion of any other elements. In addition, terms such as " . . . unit", " . . . module", or the like refer to units that perform at least one function or operation, and the units may be implemented as hardware or software or as a combination of hardware and software.

Throughout the specification, an "ultrasonic image" refers to an image of a target object obtained using an ultrasonic wave. Furthermore, in the present specification, the "target object" may include a person or an animal, or a part of a person or an animal. For example, the object may include the liver, the heart, the womb, the brain, a breast, the abdomen, or a blood vessel.

Throughout the specification, a "location of a probe" may refer to a location of a probe with respect to an object, and may refer to a coordinate point to which a probe is mapped with respect to a previously determined spatial coordinate. The "location of the probe" may refer to a distance and a direction with respect to a previously determined original point.

Furthermore, in the present specification, "user" refers to a medical professional, such as a doctor, a nurse, a medical laboratory technologist, and an engineer who repairs a medical apparatus, but the user is not limited thereto.

Embodiments of the invention now will be described more fully hereinafter with reference to the accompanying drawings, in which illustrative embodiments of the invention are shown.

FIG. 1 illustrates an ultrasonic diagnosis device 100 according to an embodiment.

Referring to FIG. 1, the ultrasonic diagnosis device 100 may include a main body 190 and a probe 102. The ultrasonic diagnosis device 100 may be connected to an auxiliary diagnosis device 200. For example, the ultrasonic diagnosis device 100 may be connected over a network to transmit and receive data such as an image of a target object and a location of a probe to and from the auxiliary diagnosis device 200.

The ultrasonic diagnosis device 100 may send an ultrasonic signal to the target object 101 through the probe 102, and receive an echo signal reflected from the target object 101. For example, the target object 101 may be a part of a patient's body such as the thyroid gland, the liver, the heart, the womb, the brain, a breast, the abdomen, or a blood vessel. The ultrasonic diagnosis device 100 may display an internal image of the target object 101 through the reflected echo signal.

The probe 102 may be connected to the main body 190 of the ultrasonic diagnosis device 100 in a wired or wireless manner. While a user scans the target object 101 via the probe 102, the probe 10 and the main body 190 may continuously transmit and receive data. The main body 190 may display the target object 101 through the data transmitted and received to and from the probe 102.

Quality of the internal image of the target object 101 may be determined according to a location of the probe 102 with respect to the target object 101. An experienced user may generally acquire an internal image of high quality due to their expertise, whereas a non-experienced user merely acquires a relatively lower quality internal image. Thus, if the experienced user remotely assists the non-experienced user in performing diagnosis, the non-experienced user may also acquire the high quality internal image.

The ultrasonic diagnosis device 100 according to an embodiment may remotely receive assistance of the auxiliary diagnosis device 200. For example, the experienced user may assist a user of the ultrasonic diagnosis device 100 in performing ultrasonic diagnosis through the auxiliary diagnosis device 200. For example, the auxiliary diagnosis device 200 may include a 3D sensor and may be a portable diagnosis device that senses the location of the probe 202. For example, the auxiliary diagnosis device 200 may be another ultrasonic diagnosis device that is remotely located with respect to the ultrasonic diagnosis device 100.

The auxiliary diagnosis device 200 may be connected to an auxiliary probe 202 having a similar shape to that of the probe 102. The auxiliary diagnosis device 200 may continuously sense a location of an auxiliary target object 201 of the auxiliary probe 202. For example, the auxiliary target object 201 may be a human model.

A location of the auxiliary probe 202 with respect to the auxiliary target object 201 may be synchronized with the location of the probe 102 with respect to the target object 101. A detailed description of a method of synchronizing the location of the auxiliary probe 202 with respect to the auxiliary target object 201 with the location of the probe 102 with respect to the target object 101 will be provided with reference to FIGS. 15 and 15 later.

The experienced user may view the image of the target object 101 received from the ultrasonic diagnosis device 100 and the location of the probe 102 and change the location of the auxiliary probe 202 that is synchronized with the probe 102. The auxiliary diagnosis device 200 may sense the changed location of the auxiliary probe 202 and transfer the sensed location to the ultrasonic diagnosis device 100. For example, the auxiliary diagnosis device 200 may transfer the location of the auxiliary probe 202 changed by synchronizing the locations of the probe 102 and the auxiliary probe 202 to the ultrasonic diagnosis device 100. For example, the auxiliary diagnosis device 200 may transfer a moving direction and a moving distance of the auxiliary probe 202 changed by synchronizing the locations of the probe 102 and the auxiliary probe 202 to the ultrasonic diagnosis device 100.

The ultrasonic diagnosis device 100 may display second location information corrected from first location information on at least one of the main body 190 and the probe 102. For example, the probe 102 may display a location correction display by using a light emitting diode (LED). The ultrasonic diagnosis device 100 may generate and display the location correction display based on a difference between the first location information and the corrected second location information. The ultrasonic diagnosis device 100 may display a moving direction, a moving distance, a scanning direction, a scanning range, a rotation direction, and a rotation angle of the probe 102.

Therefore, the user of the ultrasonic diagnosis device 100 according to an embodiment may manipulate the location of the probe 102 according to the location of the auxiliary probe 202 changed by the experienced user and acquire a high quality image. Thus, the ultrasonic diagnosis device 100 may enable the non-experienced user to easily receive assistance from the experienced user remotely.

Figure 2:
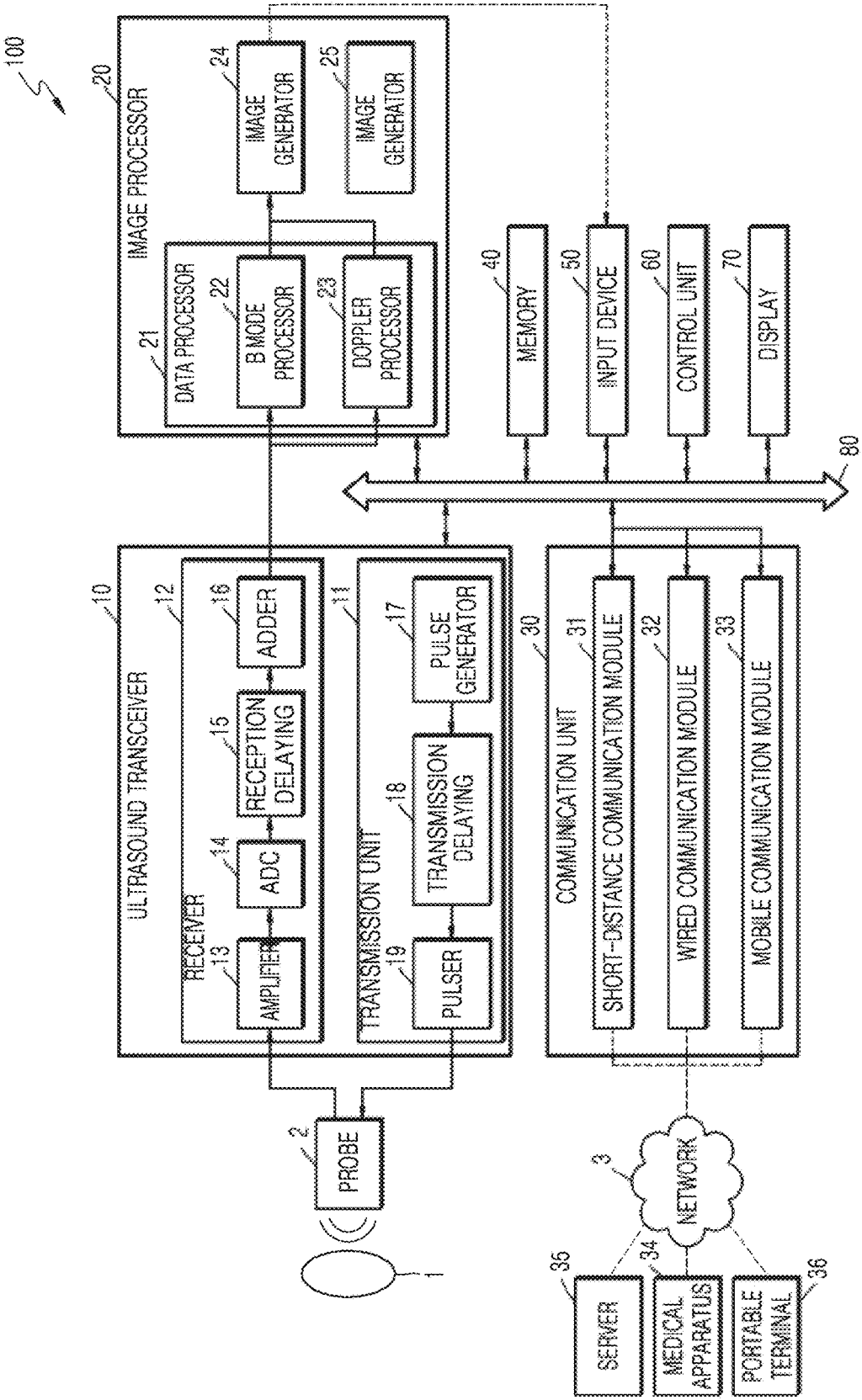
FIG. 2 is a block diagram illustrating a configuration of an ultrasonic diagnosis device according to an embodiment of the present invention.

FIG. 2 is a block diagram illustrating a configuration of the ultrasonic diagnosis device 100 according to an embodiment.

Referring to FIG. 2, the ultrasonic diagnosis device 100 may include a probe 2, an ultrasonic transceiver 10, an image processing unit 20, a communication unit 30, a memory 40, an input device 50, a control unit 60, and a display 70. The above-described elements may be connected to each other through a bus 80.

The ultrasonic diagnosis device 100 may be implemented as a portable type as well as a card type. Examples of the portable diagnosis devices may include picture archiving and communication system (PACS) viewers, smartphones, laptop computers, personal digital assistants (PDAs), tablet personal computers (PCs), etc., but are not limited thereto.

The probe 2 may irradiate an ultrasonic signal onto a target object 1 according to a driving signal applied from the ultrasonic transceiver 10, and receive an echo signal reflected from the target object 1. The probe 2 includes a plurality of transducers, which vibrate according to the applied driving signal to generate an ultrasonic wave that is sound energy. The probe 2 may be connected to a body of the ultrasonic diagnosis device 100 in a wired or wireless manner. The ultrasonic diagnosis device 100 may include a plurality of the probes 2 depending on an implementation type.

A transmission unit 11 supplies the driving signal to the probe 2, and includes a pulse generator 17, a transmission delayer 18, and a pulser 19. The pulse generator 17 generates a pulse used to generate a transmission ultrasonic wave based on a pulse repetition frequency (PRF). The transmission delayer 18 applies a delay time, used to determine a transmission directionality, to the pulse. A plurality of the pulses with the delay directionality applied thereto correspond to a plurality of piezoelectric vibrators included in the probe 2, respectively. The pulser 19 applies the driving signal (or a driving pulse) to the probe 2 at a timing corresponding to each of the pulses with the delay time applied thereto.

A reception unit 12 processes the echo signal received from the probe 2 to generate ultrasonic data, and includes an amplifier 13, an analog-to-digital converter (ADC) 14, a reception delayer 15, and an adder 16. The amplifier 13 amplifies the echo signal for each channel. The ADC 14 converts the amplified echo signal from analog to digital. The reception delayer 15 applies a delay time, used to determine a reception directionality, to the digital-converted echo signal. The adder 16 adds a plurality of the echo signals processed by the reception delayer 15 to generate the ultrasonic data. Meanwhile, the reception unit 12 may not include the amplifier 13 depending on an implementation type. In other words, if sensitivity of the probe 2 or the capability to process bit by the ADC 14 is enhanced, the amplifier 13 may be omitted.

The image processing unit 20 performs a scan conversion on the ultrasonic data generated by the ultrasonic transceiver 10 to generate an ultrasonic image. In the meantime, the ultrasonic image may include a Doppler image as a moving target object in addition to a grayscale ultrasonic image generated by scanning the target object according to the A mode, the B mode, and a motion (M) mode. The Doppler image may include a blood Doppler image (also called a color Doppler image) indicating a flow of blood, a tissue Doppler image indicating a motion of a tissue, and a spectral Doppler image that displays a moving speed of the target object as a waveform.

A B mode processing unit 22 extracts a B mode component from the ultrasonic data to process the B mode component. An image generation unit 24 may generate an ultrasonic image that displays a signal intensity as a brightness, on the basis of the B mode component extracted by the B mode processing unit 22.

Similarly, a Doppler processing unit 23 may extract a Doppler component from the ultrasonic data. The image generation unit 24 may generate a Doppler image that displays a motion of a target object as a color or a waveform, on the basis of the extracted Doppler component.

The image generation unit 24 may perform a volume rendering operation on volume data to generate a 3D ultrasonic image, and may also generate an elastic image that displays a degree of modification (based on a pressure) of the target object 1 as an image. Furthermore, the image generation unit 24 may express various pieces of additional information on the ultrasonic image as texts and graphics. The generated ultrasonic image may be stored in the memory 40.

A location confirming unit 25 may confirm a location of the probe 2 in an image of the target object 1. For example, the location confirming unit 25 may confirm a relative location of the probe 2 with respect to the target object 1 at a 3D spatial coordinate. For example, the location confirming unit 5 may confirm the relative location of the probe 2 with respect to the target object 1 by using a method that will be described with reference to FIGS. 5 through 7 later.

The communication unit 30 is connected to a network 3 in a wired or wireless manner to communicate with an external device or server. The communication unit 30 may exchange data with a hospital server or a medical apparatus of a hospital which is connected thereto through a PACS. Also, the communication unit 30 may perform data communication according to the digital imaging and communications in medicine (DICOM) standard.

The communication unit 30 may transmit and receive data, such as an ultrasonic image, ultrasonic data, Doppler data, etc. of the target object 1, associated with a diagnosis of the target object 1 over the network 3, and may also transmit and receive a medical image captured by a medical apparatus such as a computed tomography (CT) apparatus, a magnetic resonance imaging (MRI) apparatus, or an X-ray apparatus. Furthermore, the communication unit 30 may receive information on a diagnosis history or treatment schedule of a patient from a server, and use a diagnosis of the target object 1. In addition, the communication unit 30 may perform data communication with a portable terminal of a doctor or a patient, in addition to a server or medical apparatus of a hospital.

The communication unit 30 may be connected to the network 3 in a wired or wireless manner, and may exchange data with a server 35, a medical apparatus 34, or a portable terminal 36. The communication unit 30 may include one or more elements that enable communication with an external device, and may, for example, include a short-distance communication module 31, a wired communication module 32, and a mobile communication module 33.

The communication unit 30 may transmit and receive data so as to exchange information through at least one of voice calls and conference calls between users. For example, the communication unit 30 may transmit and receive data to enable a first user to receive expert knowledge regarding a diagnosis method from a second user during voice calls between users. For example, the communication unit 30 may inform users of a diagnosis status through a video screen in real time and transmit and receive data to enable the first user to receive the expert knowledge regarding the diagnosis method from the second user during conference calls between users.

The short-distance communication module 31 denotes a module for short-distance communication within a certain distance. In short-distance communication technology according to an embodiment, there may be wireless LAN, Wi-Fi, Bluetooth, Zigbee, Wi-Fi direct (WFD), ultra wideband (UWB), infrared data association (IrDA), Bluetooth low energy (BLE), and near field communication (NFC), but the short-distance communication technology is not limited thereto.

The wired communication module 32 denotes a module for communication using an electrical signal or an optical signal. Wired communication technology according to an embodiment may include a pair cable, a coaxial cable, an optical fiber cable, an Ethernet cable.

The mobile communication module 33 transmits and receives a radio frequency (RF) signal to and from at least one of a base station, an external terminal, and a server over a mobile communication network. In this regard, the RF signal may include various types of data based on transmission and reception of a voice call signal, a video call signal, or a letter/multimedia message.

The memory 40 stores various pieces of information processed by the ultrasonic diagnosis apparatus 100. For example, the memory 40 may store medical data, such as input/output ultrasonic data and ultrasonic images, associated with a diagnosis of a target object, and may also store an algorithm or a program which is executed in the ultrasonic diagnosis apparatus 100.

The memory 40 may be configured with various kinds of storage mediums such as a flash memory, a hard disk, an EEPROM, etc. Also, the ultrasonic diagnosis apparatus 100 may operate web storage or a cloud server which performs a storage function of the memory 40 on a web.

The input device 50 is used to input data by a user for controlling an operation of the ultrasonic diagnosis apparatus 100. The input device 50 may include hardware elements such as a keypad, a mouse, a touch pad, a trackball, a jog switch, but is not limited thereto. As another example, the input device 50 may further include various sensors such as an electrocardiogram (ECG) measurement module, a breath measurement sensor, a voice recognition sensor, a gesture recognition sensor, a fingerprint recognition sensor, an iris recognition sensor, a depth sensor, a distance sensor, etc.

The control unit 60 controls an overall operation of the ultrasonic diagnosis apparatus 100. That is, the control unit 60 may control operations between the probe 2, the ultrasonic transceiver 10, the image processing unit 20, the communication unit 30, the memory 40, the input device 50, the control unit 60, and the display 70.

The display 70 may display and output the generated ultrasonic image. The display 70 may display and output various types of information processed by the ultrasonic diagnosis apparatus 100 as well as the ultrasonic image through a graphic user interface (GUI). Meanwhile, the ultrasonic diagnosis apparatus 100 may include two or more displays 70 depending on an implementation type. The display 70 may display a location correction display of the probe 2 based on second location information.

The display 70 may display the location of the probe 2 as well as the ultrasonic image of the target object 1. The display 70 may display the ultrasonic image of the target object 1 along with locations of the probe 102 and the auxiliary probe 202 of FIG. 1. The display 70 may be included in the probe 102 and the auxiliary probe 202. The user may easily operate the probe 102 and the auxiliary probe 202 through the display 70. The display 70 will be described in more detail with reference to FIGS. 8, 9, and 11 later.

Some or all of the probe 2, the ultrasonic transceiver 10, the image processing unit 20, the communication unit 30, the memory 40, the input device 50, and the control unit 60 may operate via a software module, but are not limited thereto. Some of the above-described elements may operate via a hardware module. Also, at least some of the ultrasonic transceiver 10, the image processing unit 20, and the communication unit 30 may be included in the control unit 60, but are not limited in terms of implementation.

Figure 3:
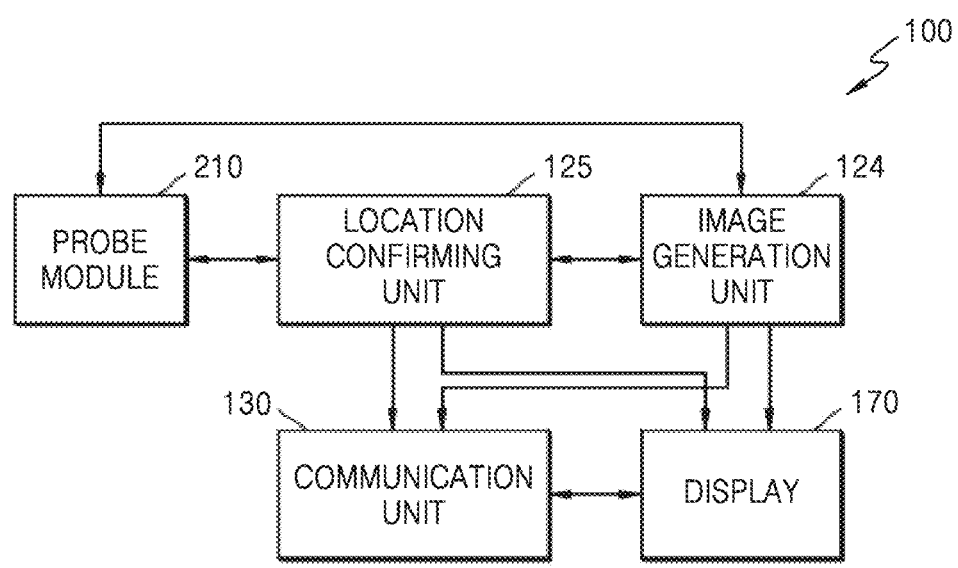
FIG. 3 is a block diagram illustrating an ultrasonic diagnosis device according to another embodiment of the present invention.

FIG. 3 is a block diagram illustrating the ultrasonic diagnosis apparatus 100 according to another embodiment.

Referring to FIG. 3, the ultrasonic diagnosis apparatus 100 may include the probe 102, a location confirming unit 125, an image generation unit 124, a communication unit 130, and a display 170. The probe 102, the location confirming unit 125, the image generation unit 124, the communication unit 130, and the display 170 of FIG. 3 may be configured in the same manner as the probe 102, the location confirming unit 25, the image generation unit 24, the communication unit 30, and the display 70 of FIG. 2, respectively.

The probe 102 may irradiate an ultrasonic signal onto a target object, and receive an echo signal reflected from the target object. The image generation unit 124 may generate an image of the target object through the received echo signal. The location confirming unit 125 may confirm a location of the probe 102 with respect to an image of the target object. The location of the probe 102 may be confirmed in various ways as will be described with reference to FIGS. 5 through 7 later.

The image generation unit 124 may generate image data of the target object diagnosed by a user. The image generation unit 124 may receive the echo signal from the probe 102, process the echo signal, and generate the image data. The image generation unit 124 may transfer a generated image to the location confirming unit 125 and the display 170. For example, the image generation unit 124 may generate a 3D ultrasonic image and transfer the generated 3D ultrasonic image to the location confirming unit 125 and the display 170.

The location confirming unit 125 may confirm location information of the probe with respect to the target object. For example, the location confirming unit 125 may receive a 3D ultrasonic image of the target object and confirm a relative location of the probe in the 3D ultrasonic image of the target object.

A method of confirming the location of the probe will be described by way of example with reference to FIGS. 5 through 7. The location of the probe may be confirmed by using other various methods. The location confirming unit 125 may transfer the confirmed location of the probe to the display 170.

The communication unit 130 may receive the image data of the target object and the location information of the probe from the image generation unit 124 and the location confirming unit 125, respectively. The communication unit 130 may transmit the received image data of the target object and location information of the probe to the outside over a network. For example, the communication unit 130 may transmit the image data and the location information to the auxiliary diagnosis device 200 of FIG. 1 over the network. The communication unit 130 may receive a location of the probe corrected by a user of the auxiliary diagnosis device 200 of FIG. 1. The communication unit 130 may receive location information of an auxiliary probe with respect to an auxiliary target object corrected by the user of the auxiliary diagnosis device 200 of FIG. 1. The communication unit 130 may transmit the location information of the auxiliary probe with respect to the auxiliary target object to the display 170.

The display 170 may receive an image of the target object and the location of the probe from the image generation unit 124 and the location confirming unit 125, respectively. The display 170 may display the location of the probe 102 with respect to the target object. The display 170 may receive and display the corrected location of the probe from the communication unit 130. The display 170 may receive and display a location of the probe corrected by an outside experienced user over the communication unit 130. The display 170 may display the location information of the auxiliary probe with respect to the auxiliary target object corrected by the user of the auxiliary diagnosis device 200 of FIG. 1.

An operation of the ultrasonic diagnosis device 100 will be described with reference to FIG. 4 below.

Figure 4:
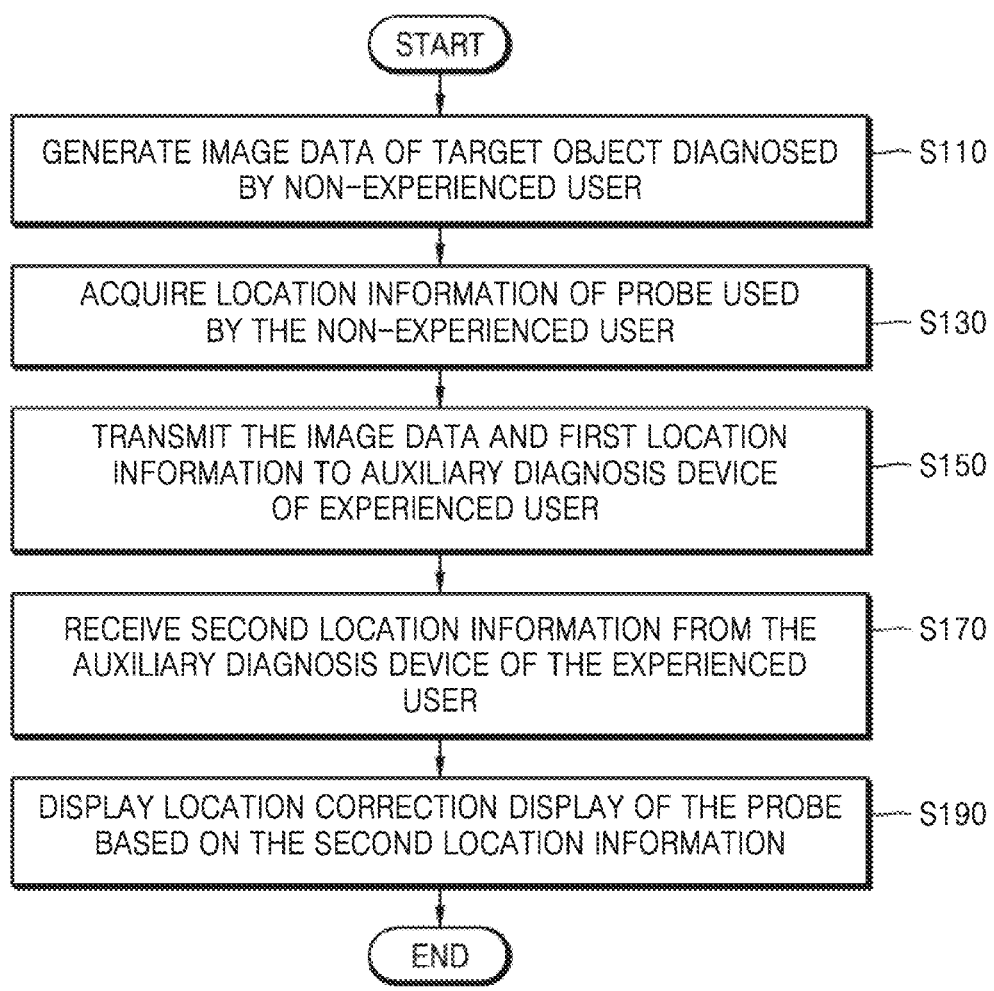
FIG. 4 is a flowchart for explaining an operation of an ultrasonic diagnosis device, according to an embodiment of the present invention.

FIG. 4 is a flowchart for explaining an operation of the ultrasonic diagnosis device 100, according to an embodiment.

Referring to FIG. 4, the ultrasonic diagnosis device 100 may generate image data of a target object diagnosed by a user (operation S110). The user of the ultrasonic diagnosis device 100 may be a non-experienced user compared to a user of the auxiliary diagnosis device 200 of FIG. 1. The ultrasonic diagnosis device 100 may receive an echo signal from the probe 102, process the echo signal, and generate image data.

The ultrasonic diagnosis device 100 may acquire location information of a probe used by the non-experienced user (operation S130). A method in which the ultrasonic diagnosis device 100 acquires the location information of the probe will be described with reference to FIGS. 5 through 7 below. The ultrasonic diagnosis device 100 may transmit the image data and first location information of the probe to an auxiliary diagnosis device of an experienced user (operation S150). The image data and the first location information of the probe may be transmitted to the auxiliary diagnosis device of the experienced user over a network and may be corrected by the experienced user.

The ultrasonic diagnosis device 100 may receive second location information from the auxiliary diagnosis device of the experienced user (operation S170). The second location information may be corrected from the first location information by the experienced user. The ultrasonic diagnosis device 100 may display a location correction display of the probe based on the second location information (operation S190).

For example, the location correction display may be determined according to a difference between the first location information of the probe and the second location information of the auxiliary probe. The location correction display may include at least one selected from the group consisting of a direction of the probe that is to move at a first location, a distance that the probe is to move, a direction in which the probe is to rotate, an angle that the probe is to rotate, a direction in which the probe is to scan, and a range within which the probe is to scan.

Therefore, the ultrasonic diagnosis device 100 according to an embodiment is configured to enable a user to easily operate with the assistance of an outside experienced user, and thus the ultrasonic diagnosis device 100 according to an embodiment may enable the user with less experience to obtain a high quality ultrasonic image.

Figure 5:
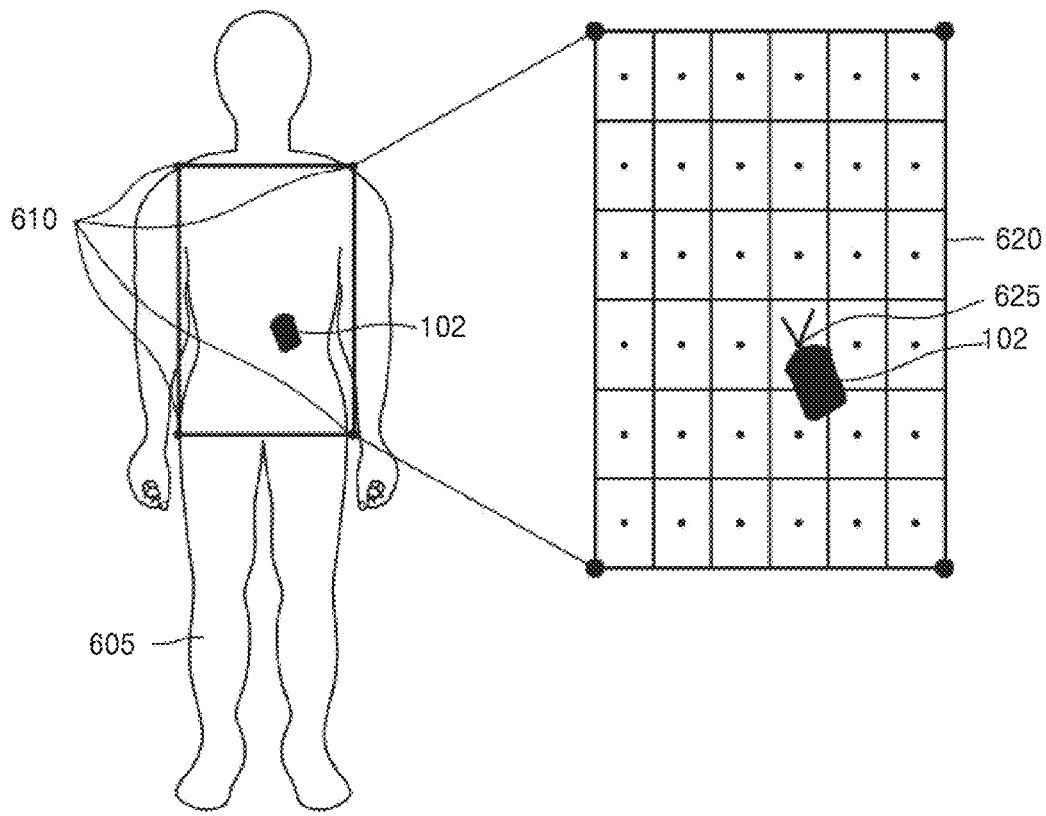
FIG. 5 is a diagram for explaining a process of confirming location information of a probe, according to an embodiment of the present invention.

FIG. 5 is a diagram for explaining a process of confirming location information of the probe 102, according to an embodiment.

The ultrasonic diagnosis device 100 may capture an examinee 605 and detect feature points 610 of the examinee 605. In the present embodiment, the ultrasonic diagnosis device 100 detects two locations of both shoulders of the examinee 605 and two locations of both pelvises thereof as the feature points 610. However, the locations are merely examples and are not limited to the description provided above.

The ultrasonic diagnosis device 100 acquires a bone structure 620 of the examinee 605 by connecting the feature points 610. In the present embodiment, the ultrasonic diagnosis device 100 may recognize a square obtained by connecting the feature points 610 as the bone structure 620 of the examinee 605.

Thereafter, the ultrasonic diagnosis device 100 splits the skeletal bone structure 620 into a plurality of segments. In the present embodiment, the ultrasonic diagnosis device 100 splits the bone structure 620 into rectangular segments in a 6×6 alignment, but the splitting is not limited thereto. The ultrasonic diagnosis device 100 may split the bone structure 620 into less or more segments or in a continuous alignment of triangular and inverted triangular segments rather than the rectangular segments.

Meanwhile, the ultrasonic diagnosis device 100 may select one of the plurality of segments as location information of the probe 102 by using the detected location of the probe 102. In the present embodiment, the ultrasonic diagnosis device 100 may match the location information of the probe 102 with respect to a segment 625. Accordingly, the ultrasonic diagnosis device 100 may reduce an error of the location information of the probe 102 and may measure an accurate location of the probe 102 with respect to an examinee.

FIGS. 6A and 6B are diagrams for explaining a process of acquiring location information of the probe 102, according to an embodiment.

As described above, as another embodiment in which the ultrasonic diagnosis device 100 acquires location information of the probe 102, a 3D modeling process or an image comparison process may be used.

Referring to FIG. 6A, the ultrasonic diagnosis device 100 captures a hand of a user 710 holding the probe 102 and an examinee 705. Thereafter, the ultrasonic diagnosis device 100 applies a 3D labeling algorithm to a captured image. As a result, the ultrasonic diagnosis device 100 may separately recognize the examinee 705, the user 710, and the probe 102. Thereafter, the ultrasonic diagnosis device 100 may track the recognized probe 102 and change and determine a diagnosis part according to a path along which the probe 102 moves.

Referring to FIG. 6B, the ultrasonic diagnosis device 100 may generate a first image 720 obtained by capturing an image of an examinee 715 before the user diagnoses the examinee 815 by using the probe 102. Thereafter, the ultrasonic diagnosis device 100 may generate a second image 730 obtained by capturing an image of the probe 102 and the examinee 715 together and compare the first image 720 and the second image 730. Through the above-described image comparison process, the ultrasonic diagnosis device 100 may separately recognize the probe 102.

Figure 7A:
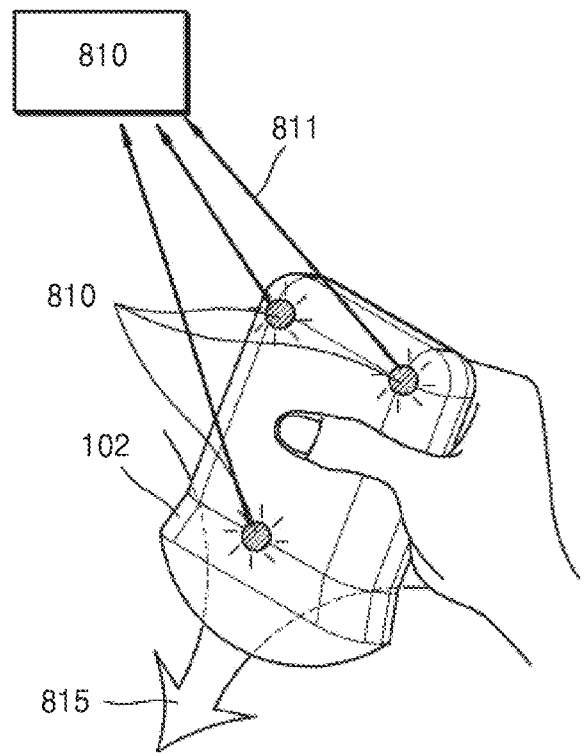
FIGS. 7A and 7B are diagrams for explaining a process of acquiring location information of a probe, according to another embodiment of the present invention.
Figure 7B:
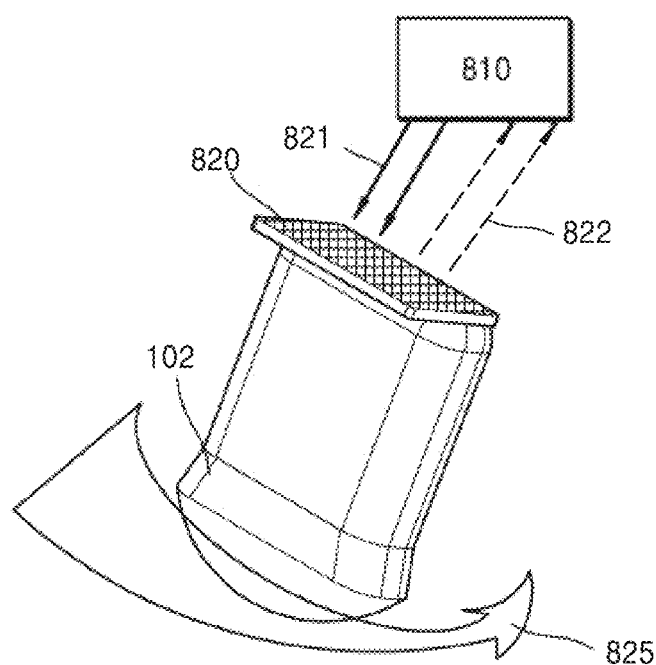

FIGS. 7A through 7C are diagrams for explaining a process of acquiring location information of the probe 102, according to another embodiment.

Referring to FIG. 7A, an example of acquiring the location information of the probe 102 by using an infrared LED 810 is illustrated. An infrared capturing unit 810 of the ultrasonic diagnosis device 100 receives an infrared signal 811 transmitted from the infrared LED 810 that is attached onto the probe 102. Thereafter, the ultrasonic diagnosis device 100 may analyze the received infrared signal 811 and acquire the location information of the probe 102. For example, the ultrasonic diagnosis device 100 may acquire spatial coordinates of three center locations of the infrared LED 810 as the location information of the probe 102.

Meanwhile, the ultrasonic diagnosis device 100 may acquire information regarding a movement of the probe 102 such as a moving direction, a scan direction, and a rotation direction of the probe 102, in addition to the location information of the probe 102. That is, the ultrasonic diagnosis device 100 may detect a location to which the probe 102 is moved and a direction in which the probe 102 rotates according to changes of the three center locations of the infrared LED 810 attached onto the probe 102.

In the present embodiment, the user moves the probe 102 in a direction of an arrow 815 and scans an examinee. Accordingly, the ultrasonic diagnosis device 100 detects the changes of the three center locations of the infrared LED 810, thereby measuring the moving direction and the scan direction of the probe 102.

Referring to FIG. 7B, an example of acquiring the location information of the probe 102 by using a reflection sheet 820 is illustrated. The infrared capturing unit 810 of the ultrasonic diagnosis device 100 sends an infrared signal 821 and receives a reflection signal 822 reflected from the reflection sheet 820 attached onto the probe 102. Thereafter, the ultrasonic diagnosis device 100 analyzes the reflection signal 822, thereby acquiring the location information of the probe 102.

Meanwhile, as described with reference to FIG. 7A above, the ultrasonic diagnosis device 100 may acquire information regarding a movement of the probe 102 along with the location information of the probe 102. In the present embodiment, a pattern used to generate the reflection signal 822 may be previously formed on the reflection sheet 820. Accordingly, the ultrasonic diagnosis device 100 may detect a movement and a rotation of the pattern formed on the reflection sheet 820 and may measure the movement of the probe 102. In the present embodiment, the ultrasonic diagnosis device 100 detects the rotation of the reflection sheet 820, thereby measuring the movement of the probe 102 that rotates in a direction of an arrow 825.

Figure 8:
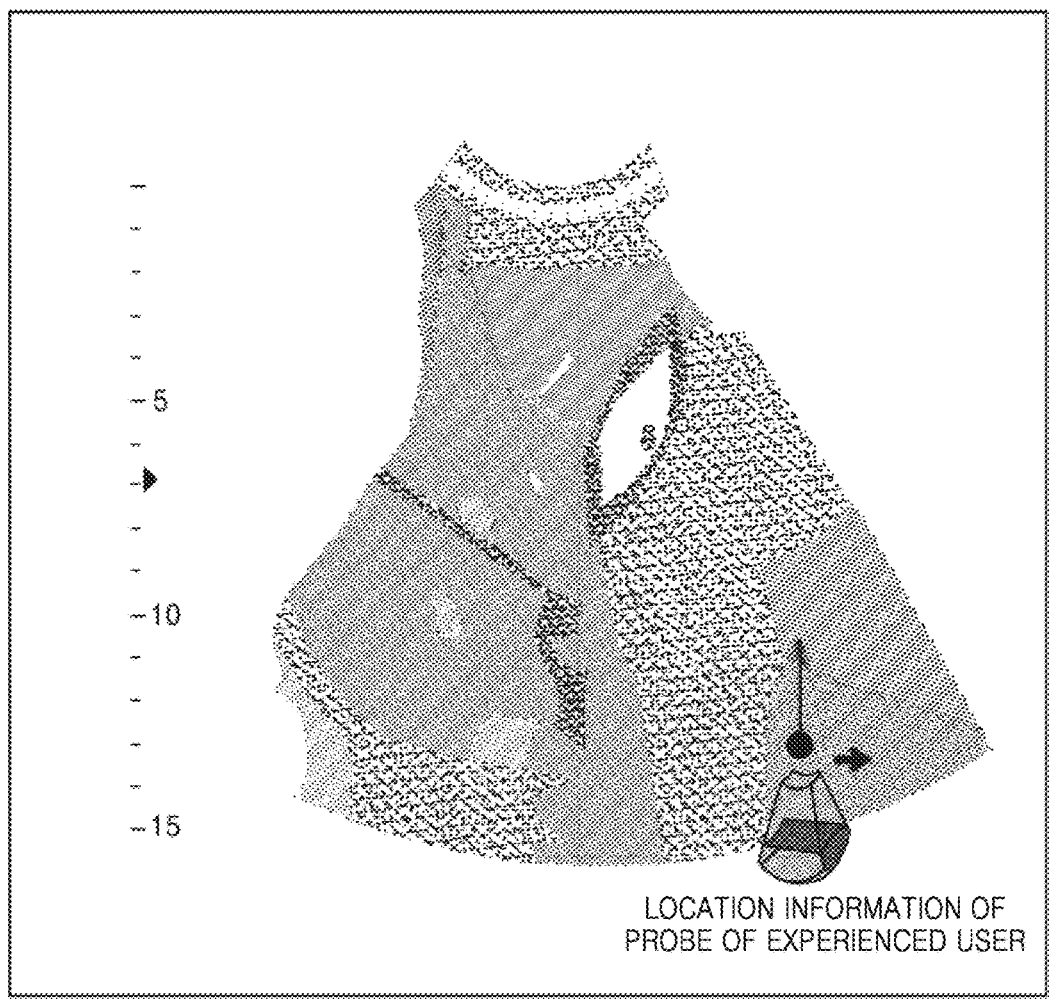
FIGS. 8 and 9 are diagrams illustrating location information of a probe being displayed in an image of a target object on a display of an ultrasonic diagnosis device, according to embodiments of the present invention.
Figure 9:
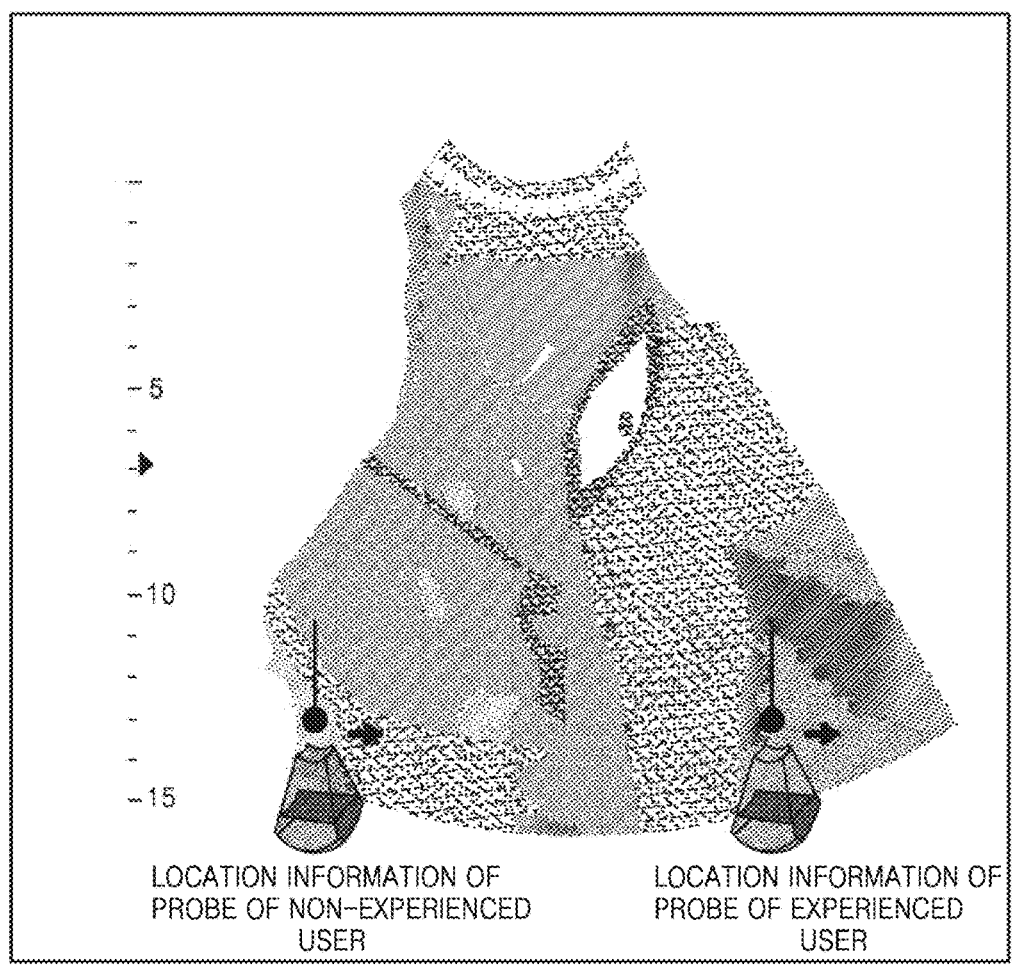

FIGS. 8 and 9 are diagrams illustrating location information of a probe 102 being displayed in an image of a target object on the display 170 of the ultrasonic diagnosis device 100, according to embodiments.

Referring to FIG. 8, the display 170 of the ultrasonic diagnosis device 100 may display location information of the auxiliary probe 202 (of FIG. 1) of an experienced user. Referring to FIG. 9, the display 170 of the ultrasonic diagnosis device 100 may display location information of the probe 102 (of FIG. 1) of a non-experienced user and the location information of the auxiliary probe 202 (of FIG. 1) of the experienced user. The location information of the auxiliary probe 202 may display only a relative location with respect to the location information of the probe 102 (of FIG. 1). For example, the location information of the auxiliary probe 202 may include at least one selected from the group consisting of a moving direction that is to be corrected, a moving distance, a scan direction, a scan range, a rotation direction, and a rotation angle, with respect to the location information of the probe 102 (of FIG. 1).

Figure 10:
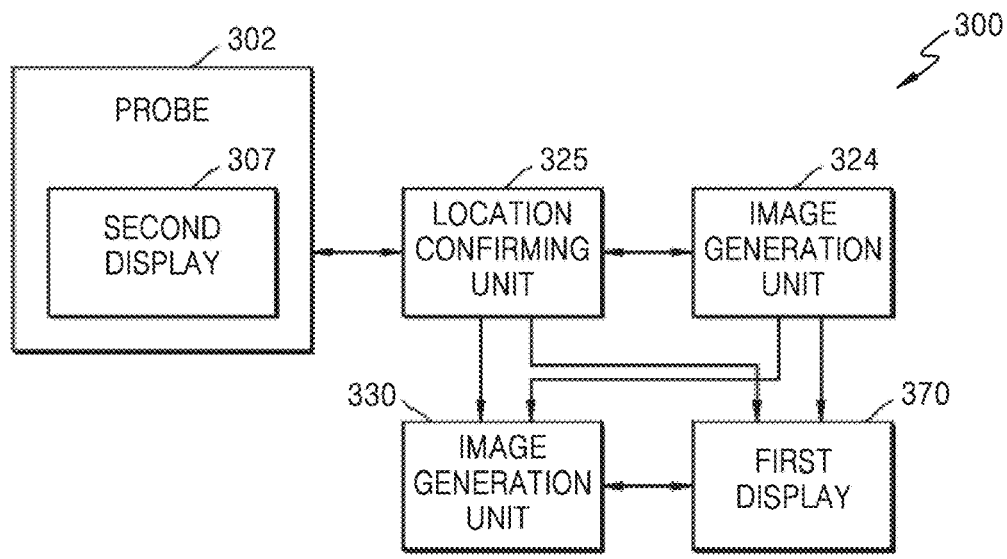
FIG. 10 is a block diagram illustrating an ultrasonic diagnosis device according to another embodiment of the present invention.

FIG. 10 is a block diagram illustrating an ultrasonic diagnosis device 300 according to another embodiment.

Referring to FIG. 10, the ultrasonic diagnosis device 300 may include a probe 302, a location confirming unit 325, an image generation unit 324, a communication unit 330, and a first display 370. The probe 302, the location confirming unit 325, the image generation unit 324, the communication unit 330, and the first display 370 of the present embodiment may be configured in the same manner as the probe 102, the location confirming unit 125, the image generation unit 124, the communication unit 130, and the display 170 of FIG. 3. Redundant descriptions will not be repeated below.

Figure 11:
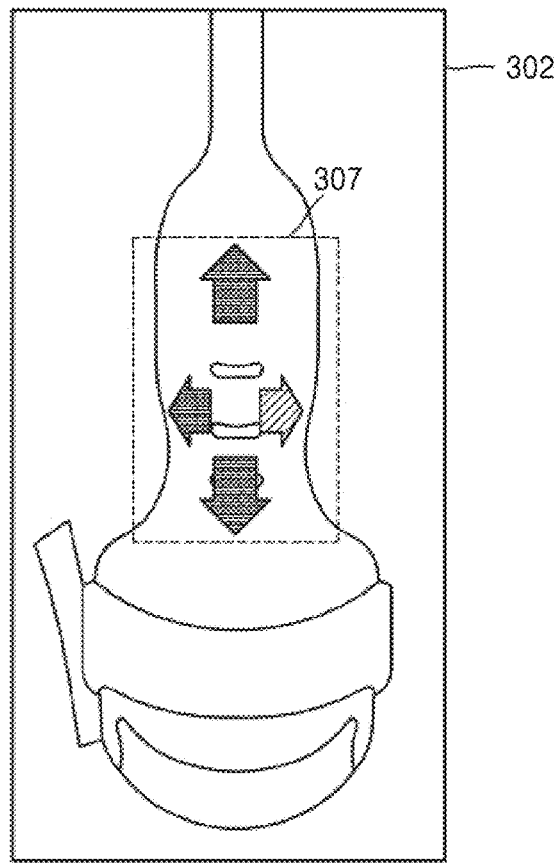
FIG. 11 is a diagram of a probe including a second display, according to an embodiment of the present invention.

The probe 302 of the ultrasonic diagnosis device 300 according to another embodiment may include a second display 307. For example, the probe 302 may include the second display 307 as shown in FIG. 11. For example, the second display 307 may display a moving direction that is to be corrected, with respect to location information of the probe 102 (of FIG. 1) by using a LED.

For example, the second display 307 may include a flat panel display device including a liquid crystal display (LCD) or the LED, or a flat panel display device including a touch screen device. Thus, the ultrasonic diagnosis device 300 may enable a user to more easily acquire an ultrasonic image.

Figure 12:
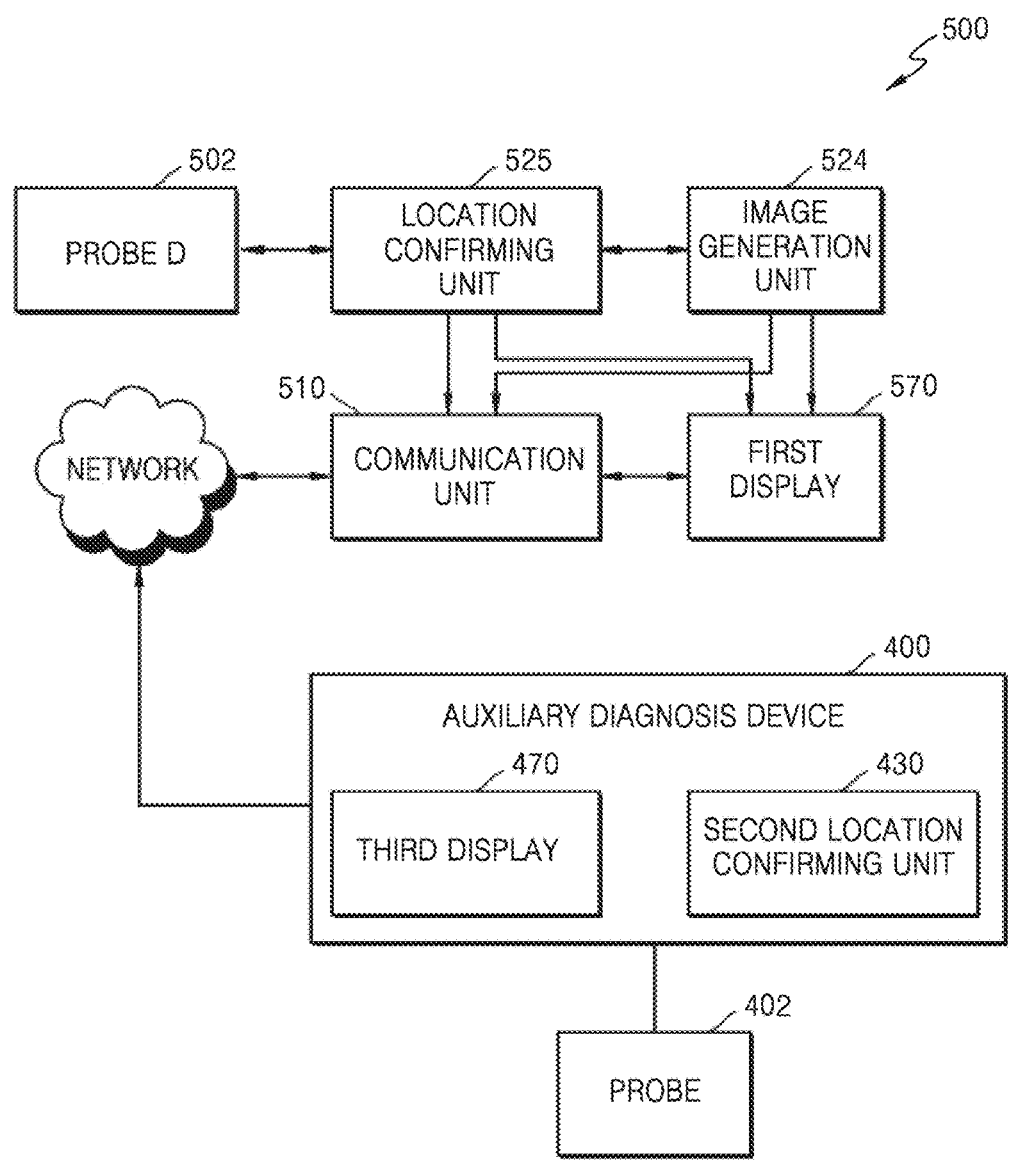
FIG. 12 is a block diagram illustrating an ultrasonic diagnosis device according to another embodiment of the present invention.

FIG. 12 is a block diagram illustrating an ultrasonic diagnosis device 500 according to another embodiment.

Referring to FIG. 12, the ultrasonic diagnosis device 500 may include a probe 502, a location confirming unit 525, an image generation unit 524, a communication unit 530, and a first display 570. The probe 502, the location confirming unit 525, the image generation unit 524, the communication unit 530, and the first display 570 of the present embodiment may be configured in the same manner as the probe 102, the location confirming unit 125, the image generation unit 124, the communication unit 130, and the display 170 of FIG. 3. Redundant descriptions will not be repeated below.

The ultrasonic diagnosis device 500 according to an embodiment may be connected to an auxiliary diagnosis device 400 over a network. The network may include various wired and wireless communication environments. The auxiliary diagnosis device 400 may include a third display 470 and a second location confirming unit 430.

The third display 470 may display image data generated by the image generation unit 524 and location information of the probe 502. The third display 470 may display location information of the auxiliary target object 201 of an auxiliary probe along with the image data generated by the image generation unit 524 and the location information of the probe 502. The third display 470 may display the same image as that displayed on the first display 570.

The second location confirming unit 430 may confirm a location of the auxiliary probe 402, generate location information of an auxiliary probe 402, and transfer the location information of the auxiliary probe 402 to the third display 470 and a network. The second location confirming unit 430 may generate location information of an auxiliary probe 502 by using the same method of confirming the location of the probe as described with reference to FIGS. 5 through 7 above.

Operations of the ultrasonic diagnosis device 500 and the auxiliary diagnosis device 400 will now be described with reference to FIG. 13 below.

FIG. 13 is a flowchart for explaining operations of the ultrasonic diagnosis device 500 and the auxiliary diagnosis device 400, according to an embodiment.

The ultrasonic diagnosis device 500 synchronizes a location of the probe 502 and a location of the auxiliary probe 402 (operation S210). A method in which the ultrasonic diagnosis device 500 synchronizes the location of the probe 502 and the location of the auxiliary probe 402 will be described with reference to FIGS. 14 and 15 later.

The ultrasonic diagnosis device 500 generates image data of a target object diagnosed by a non-experienced user (operation S220). The ultrasonic diagnosis device 500 confirms a first location of the probe 502 with respect to the target object and generates first location information (operation S230). The ultrasonic diagnosis device 500 transfers the image data of the target object and the first location of the probe 502 to the auxiliary diagnosis device 400. The auxiliary diagnosis device 400 may display the received image data of the target object and location of the probe 502 (operation S240). The auxiliary diagnosis device 400 may confirm second location information of the auxiliary probe 402 (operation S250). The auxiliary diagnosis device 400 may transfer the second location information of the auxiliary probe 402 to the ultrasonic diagnosis device 500. The ultrasonic diagnosis device 500 may display a location correction display of the probe 502 based on the second location information (operation S260). The ultrasonic diagnosis device 500 may confirm whether the location of the probe 502 has been changed in accordance with a second location of the auxiliary probe 402 (operation S270). Operations S220 through S270 may be repeatedly performed until the location of the probe 502 with respect to the target object is identical to that of the auxiliary probe 402 with respect to an auxiliary target object.

FIGS. 14A and 15C are diagrams for explaining a process of synchronizing a location of a probe and a location of an auxiliary probe, according to an embodiment.

Referring to FIGS. 14A through 14C, an ultrasonic diagnosis device may confirm a measurement location of a patient by using a camera. The ultrasonic diagnosis device may confirm the measurement location of the patient through an image captured by the camera and generate a more detailed image with respect to the measurement location of the patient.

For example, the ultrasonic diagnosis device may confirm the measurement location of the patient as shown in FIGS. 14A through 14C. The camera included in the ultrasonic diagnosis device may automatically focus the location of the probe, may zoom in on the measurement location of the patient in more detail with respect to the location of the probe, and may generate an image.

The image generated by the camera of the ultrasonic diagnosis device may be transmitted to an auxiliary diagnosis device over a network as illustrated in FIG. 12. A user of the auxiliary diagnosis device may set an initial location of the auxiliary probe through the image received over the network.

Referring to FIGS. 15A through 15C, the ultrasonic diagnosis device may confirm the measurement location of the patient without the camera. The ultrasonic diagnosis device may confirm the measurement location of the patient through a conceptualized image or a body marker. The ultrasonic diagnosis device may confirm the measurement location of the patient through the conceptualized image or the body marker and may zoom in on the measurement location of the patient in more detail.

For example, the ultrasonic diagnosis device may confirm the measurement location of the patient through the conceptualized image or the body marker, may zoom in on the measurement location of the patient in more detail, and may generate an image as shown in FIGS. 15A through 15C. The image generated by the ultrasonic diagnosis device may be transmitted to the auxiliary diagnosis device over the network as illustrated in FIG. 12. A user of the auxiliary diagnosis device may set an initial location of the auxiliary probe through the image received over the network.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An ultrasonic diagnosis system comprising:
an auxiliary diagnosis device having an auxiliary probe, and
an ultrasonic diagnosis device including:
a first probe;

a memory storing instructions;
at least one processor configured to execute the instructions stored in the memory to perform functions to:
generate image data of a target object diagnosed by a first user based on ultrasonic signals transmitted to the target object from the first probe; and
confirm a first physical location of the first probe with respect to the target object;
a wired or wireless network communication transceiver performing functions to:
transmit the image data and information on the first physical location to the auxiliary diagnosis device distinct from the ultrasound diagnosis device across a wired or wireless network; and
receive, across the wired or wireless network from the auxiliary ultrasonic diagnosis device, information on a second physical location of the auxiliary probe of the auxiliary diagnosis device with respect to an auxiliary target object; and
an image processor controlling a display and executing instructions to cause the display to perform functions to display a location correction of the first probe wherein the location correction is a correlation between the first physical location of the first probe of the first ultrasonic diagnosis device and the second physical location of the auxiliary probe of the auxiliary ultrasonic diagnosis device, and the display of the location correction of the first probe includes the display of a location of the first probe that needs to be corrected as at least one selected from the group consisting of a moving direction, a moving distance, a scan direction, a scan range, a rotation direction, and a rotation angle.

2. The ultrasonic diagnosis system of claim 1, wherein the second physical location is determined according to a movement of the auxiliary probe adjusted by a second user.

3. The ultrasonic diagnosis system of claim 2, wherein the auxiliary probe comprises a three-dimensional (3D) sensor that tracks a movement of the auxiliary probe.

4. The ultrasonic diagnosis system of claim 1, wherein the display is included in at least one of the first probe and a body of the ultrasonic diagnosis device.

5. The ultrasonic diagnosis system of claim 1, wherein the image data of the target object is 3D image data.

6. The ultrasonic diagnosis system of claim 1, further comprising:
a camera enabling the first user to capture an image used to diagnose the target object in real time.

7. The ultrasonic diagnosis system of claim 6, wherein the wired or wireless network communication transceiver transmits the image to be used for diagnosis by the first user.

8. The ultrasonic diagnosis system of claim 6, wherein the camera zooms in on the image to be used for diagnosis by the first user with respect to a location of the first probe.

9. The ultrasonic diagnosis system of claim 1, wherein the wired or wireless network communication transceiver transmits the information on the first physical location of the first probe in an image of the target object in real time.

10. The ultrasonic diagnosis system of claim 1, wherein the display displays the first location information of the first probe and the second location information of the auxiliary probe.

11. The ultrasonic diagnosis system of claim 1, wherein the wired or wireless network communication transceiver transmits and receives data to enable users to exchange information through at least one of a voice call and a conference call.

12. An ultrasonic diagnosis method comprising:
generating image data of a target object based on ultrasonic signals transmitted to the target object from a first probe of a first ultrasonic diagnosis device;
confirming a first physical location of the first probe with respect to the target object;
transmitting the image data and information on the first physical location to an auxiliary diagnosis device distinct from the ultrasound diagnosis device across a wired or wireless network;
receiving, across the wired or wireless network from the auxiliary ultrasonic diagnosis device, information on a second physical location of an auxiliary probe of the auxiliary ultrasonic diagnosis device with respect to an auxiliary target object; and
displaying, on a display of the ultrasonic diagnosis device, a location correction of the first probe wherein the location correction is a correlation between the first physical location of the first probe of the first ultrasonic diagnosis device and the second physical location of the auxiliary probe of the auxiliary ultrasonic diagnosis device,
wherein the displaying of the location correction of the first probe comprises displaying a location of the first probe that needs to be corrected as at least one selected from the group consisting of a moving direction, a moving distance, a scan direction, a scan range, a rotation direction, and a rotation angle.

13. The ultrasonic diagnosis method of claim 12, wherein the second physical location is determined according to a movement of the auxiliary probe adjusted by a second user.

14. The ultrasonic diagnosis method of claim 12, wherein the image data of the target object is 3D image data.

15. The ultrasonic diagnosis method of claim 12, further comprising:
displaying the first physical location information of the first probe and the second physical location information of the auxiliary probe.

16. A non-transitory computer readable recording medium having recorded thereon a program for executing the ultrasonic diagnosis method of claim 12.

* * * * *